(12) United States Patent
Leonard et al.

(10) Patent No.: US 7,229,640 B2
(45) Date of Patent: Jun. 12, 2007

(54) PAROXETINE CONTROLLED RELEASE COMPOSITIONS

(75) Inventors: Graham Stanley Leonard, St. Albans (GB); David Philip Elder, Hertford (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/024,858

(22) Filed: Dec. 18, 2001

(65) Prior Publication Data

US 2002/0090394 A1 Jul. 11, 2002

Related U.S. Application Data

(63) Continuation of application No. 09/391,796, filed on Sep. 9, 1999, which is a continuation of application No. 08/817,911, filed as application No. PCT/EP96/03252 on Jul. 19, 1996, now abandoned.

(30) Foreign Application Priority Data

Jul. 20, 1995 (GB) .............................................. 9514842

(51) Int. Cl.
*A61K 9/20* (2006.01)
*A61K 9/22* (2006.01)
*A61K 9/24* (2006.01)
A61K 9/28; A61K 9/32

(52) U.S. Cl. ........................ 424/464; 424/465; 424/468; 424/472; 424/474; 424/482

(58) Field of Classification Search ................. 424/464, 424/465, 468, 472, 474, 482, 451, 457, 475, 424/476, 484, 458, 459
See application file for complete search history.

(56) References Cited

U.S. PATENT DOCUMENTS

| | | | |
|---|---|---|---|
| 3,536,809 A | 10/1970 | Appleweig | |
| 3,598,123 A | 8/1971 | Zaffaroni | |
| 3,630,200 A | 12/1971 | Higuchi | |
| 3,845,770 A | 11/1974 | Theeuwes et al. | |
| 3,916,899 A | 11/1975 | Theeuwes et al. | |
| 4,007,196 A | 2/1977 | Christensen et al. | |
| 4,008,719 A | 2/1977 | Theeuwes et al. | |
| 4,085,225 A | 4/1978 | Welle et al. | |
| 4,314,081 A | 2/1982 | Molloy et al. | |
| 4,444,778 A | 4/1984 | Coughlin | |
| 4,536,518 A | 8/1985 | Welch, Jr. et al. | |
| 4,615,697 A | 10/1986 | Robinson | |
| 4,721,723 A | 1/1988 | Barnes et al. | |
| 4,797,286 A | 1/1989 | Thakkar et al. | |
| 4,804,669 A | 2/1989 | Lassen | |
| 4,839,177 A | 6/1989 | Colombo et al. | |
| 4,847,092 A | 7/1989 | Thakkar et al. | |
| 4,851,228 A | 7/1989 | Zentner et al. | |
| 4,988,679 A | 1/1991 | Chavkin et al. | |

(Continued)

FOREIGN PATENT DOCUMENTS

| | | |
|---|---|---|
| CA | 2 031 393 | 12/1989 |
| CA | 1 298 479 | 4/1992 |
| CA | 2 143 070 | 12/2001 |
| EP | 0 269 303 | 11/1987 |
| EP | 0 449 562 A2 | 3/1991 |
| EP | 0 432 607 B1 | 6/1991 |
| EP | 0 546 593 | 10/1992 |
| EP | 0 654 263 | 11/1994 |
| EP | 0 714 663 | 6/1996 |
| JP | 4 036 237 | 2/1992 |
| JP | 5 139 964 | 6/1993 |
| WO | WO 91/13612 | 9/1991 |
| WO | WO 92/03124 | 3/1992 |
| WO | 92/09281 * | 6/1992 |
| WO | WO 92/13452 | 8/1992 |
| WO | WO 92/19226 | 11/1992 |
| WO | WO 93/09769 | 5/1993 |
| WO | WO 93/24154 | 12/1993 |
| WO | WO 94/10990 | 5/1994 |
| WO | 95/15155 * | 6/1995 |
| WO | WO 95/16448 | 6/1995 |
| WO | WO 95/19956 | 7/1995 |
| WO | WO 95/20964 | 8/1995 |
| WO | WO 95/30422 | 11/1995 |
| WO | WO 96/02240 | 2/1996 |
| WO | WO 96/14059 | 5/1996 |
| WO | WO 96/31197 | 10/1996 |
| WO | WO 96/33165 | 10/1996 |
| WO | WO 96/33166 | 10/1996 |
| WO | WO 97/02037 | 1/1997 |
| WO | WO 97/02239 | 1/1997 |
| WO | WO 97/03966 | 2/1997 |
| WO | WO 97/18798 | 5/1997 |
| WO | WO 97/26257 | 7/1997 |
| WO | WO 97/43249 | 11/1997 |
| WO | WO 98/43959 | 10/1998 |

OTHER PUBLICATIONS

Chemical Abstracts, 124(10), Abstract No. 127144, XP002018196 (1996), See Abstract and CA, A2143070 (P.MODI) (1995).
Rickels, et al., J. Clin. Psychiatry, vol. 51(12) Suppl. B (1990).
Willner, Psychopharmacology, vol. 85, pp. 387–404 (1985).
Drug Facts and Compounds, pp. 1325, 1994 Edition.
Remington's Pharmaceutical Sciences, 18th Edition, Mack Publishing Company, Cover Page and pp. 1676 to 1686 of Chapter 91 (1990).
Remington's Pharmaceutical Sciences, 19th Edition, Mack Publishing Company, Cover Page and pp. 1660, 1662, 1664 and 1665 of Chapter 94 Date?.

(Continued)

*Primary Examiner*—Humera N. Sheikh
(74) *Attorney, Agent, or Firm*—Wayne J. Dustman; Stephen Venetianer

(57) ABSTRACT

A controlled release or delayed release formulation contains a selective serotonin reuptake inhibitor (SSRI) such as paroxetine.

2 Claims, No Drawings

U.S. PATENT DOCUMENTS

| | | | |
|---|---|---|---|
| 4,996,358 | A | | 2/1991 | Handa et al. |
| 5,102,666 | A | | 4/1992 | Acharya |
| 5,110,605 | A | | 5/1992 | Acharya |
| 5,151,434 | A | | 9/1992 | Irikura et al. |
| 5,271,946 | A | | 12/1993 | Hettche |
| 5,284,662 | A | | 2/1994 | Koparkar et al. |
| 5,322,697 | A | | 6/1994 | Meyer |
| 5,371,092 | A | | 12/1994 | Johnson |
| 5,422,123 | A | * | 6/1995 | Conte et al. |
| 5,668,134 | A | | 9/1997 | Limstra et al. |
| 5,686,094 | A | | 11/1997 | Acharya |
| 5,776,969 | A | | 7/1998 | James |
| 5,811,436 | A | | 9/1998 | Leonard et al. |
| 6,133,289 | A | | 10/2000 | Ward et al. |
| 6,168,805 | B1 | | 1/2001 | Hein et al. |

OTHER PUBLICATIONS

Caley, et al., The Annals of Pharmacology, 1993, vol. 27, pp. 1212–1222.
FDA FOIA Materials, Jun. 1993.
Lund, et al., Acta. Pharmacol. Toxicol., 1979, vol. 44, pp. 289–295.
Torii, et al., Naunyn–Schmiedeberg's Arch. Pharmacol., 1991, vol. 344, pp. 564–567.
Gale, J. of Pediatric Gast. and Nutrition, 1995, vol. 21, Suppl. 1, pp. S22–S28.
Bailey, et al., J. of Psychopharm., 1995, vol. 9, No. 2, pp. 137–141.
Finley, The Annals of Pharmacotherapy, 1994, vol. 28, pp. 1359–1369.
J. van Harten, et al., Neuropsychopharmacology, 1994, vol. 10, No. 35, pp. 104S.
Chambers Science and Technology Dictionary, 1994.
Duboff, J. Clin. Psychopharmacology, 1993, vol. 13, No. 6, pp. 28S–33S.
Conte, et al., Travaux Originaux Reserach Papers, Sep. 1993.
Conte, et al., J. of Controlled Release, 1993, vol. 26, pp. 39–47.
Harten, et al., Clin. Pharmacokinet, 1993, vol. 24, No. 2, pp. 177–182.
Bergeron, et al., Am. J. Psychiatry, 1994, vol. 151, No. 7, pp. 1084–1086.
Dunner, et al., J. Clin. Psychiatry, 1992, vol. 53, No. 2, pp. 21–22.
Golden, Psychoopharmacology Bulletin, 2003, vol. 37, Supp. 1, pp. 176–186.
Turkish Application No. TR99/317, Examination Report (translation) 1980.
Opposition to Israeli Appl. No. 122940, Unipharm LTD v. SmithKline Beecham, Jan. 2002.
Remington's Pharma Sciences, Editorial Panamerica Co., 1980 (17$^{th}$ edition)–(translation).
Opposition to European Patent No. EP 0839039, (Aug. 5, 2004) by Solvay Pharmaceuticals, Netherlands.
Opposition to European Patent No. EP 0839039. (Aug. 4, 2004) by Dragotti & Associati SRL, Italy.
Aulton, Ed., "Pharmaceutics: The Science of Dosage form Design", pp. 204–211, Churchill Livingstone, Edinburgh (1998).
Leonard; *J Clin Psychiatry, 1993 Aug; 54 Suppl: 3–15; discussion*.
Leonard: *Drugs 1992; 43 Suppl 2:3–9; discussion 9–10*.
Jenner; *Int Clin Psychopharmacol. 1992 Jun.; 6 Suppl 4: pp. 69–80*.
De Wilde et al., *Acta Psychiatr Scand. 1993 Feb; 87(2): pp. 141–5*.
Boyer & Feighner; *J Clin Psychiatry, 1992 Feb; 53 Suppl: pp. 3–6*.
Dechant & Clissold; *Drugs 1991 Feb; 41(2): pp. 225–53*.
Lucchelli et al., *Br J Pharmacol., 1995 Mar; 114(5): pp. 1017–25*.
Sanger & McClelland; *Eur J Pharmacol. 1986 Aug 15: 127(3): pp. 179–85*.
Chambliss et al., *J Pharma Sci. 1984 Sep; 73(9): pp. 1215–9*.
Ryan et al., *Clin Pharmacol Ther. 1987 Jul; 42(1): pp. 28–32*.
Hawthorne et al., *Br J Clin Pharmacol. 1991 Jul; 32(1): pp. 77–83*.
Aabakken et al., *Scand J Gastroenterol Suppl. 1989; 163: pp. 65–73*.
Florence & Jani; *Drug Saf. 1994 Mara; 10(3): pp. 233–66*.
Mori et al., *J Pharm Sci 1991 Sep; 80(9): pp. 876–80*.
Lucker et al., *Arzneimittelforschung. 1982; 32(4): pp. 409–13*.
Fara et al., *Pharm Res. 1988 Mar*; 5(3): pp. 165–71.
Perucca et al, Clin Pharmacokinet (1994) 27(3): pp. 175–190.
ABPI Data Sheet Compendium 1988–89, pp. 445–6.
Freeman, J Psychiatr Neurosci, vol. 16 No. 2 (Suppl 1), 1991.
Synopsis section of Clinical Trials, Apr. 06, 1998, pp. 1–11.
Synopsis section of Clinical Trials, Dec. 03, 1997, pp. 1–9.
Synopsis section of Clinical Trials, Dec. 04, 1997, pp. 1–9.
Opposition to European Patent No. EP–B–0839039 dated Aug. 4, 2006.
Lee & Robinson, 1978, Chapter 3 "Methods to achieve sustained drug delivery", pp. 150 and 176–178.
Remington: The Science and Practice of Pharmacy, vol. II, 1995, Chapter 71, pp. 1189–1195.
Remington: The Science and Practice of Pharmacy, vol. II, 1995, Chapter 94, pp. 1660–1675.
Final Clinical Report 29060/451, Mar. 18, 1996, pp. 1–42.
Final Clinical Report 29060/474, Oct. 17, 1997, pp. 1–48.
Final Clinical Report 29060/452, Apr. 17, 1996, pp. I–XVIII, 1–34 and 171–182.
Rapaport, et al., J. Clin. Psychiatry, 2003, vol. 64, pp. 1065–1074.
Golden, et al., J. Clin. Psychiatry, 2002, vol. 63, pp. 577–584.
DeVane, J. Clin. Psychiatry, 2003, vol. 64, Suppl. 18, pp. 14–19.
Nemeroff, J. Clin. Psychiatry, 2003, vol. 64, Suppl. 18, p. 25–30.

* cited by examiner

PAROXETINE CONTROLLED RELEASE COMPOSITIONS

This is a continuation of application Ser. No. 09/391,796, filed Sep. 9, 1999, which is a continuation of application Ser. No. 08/817,911 filed Aug. 26, 1997, now abandoned which is a §371 of PCT/EP96/03252, filed Jul. 19, 1996.

The present invention relates to a novel formulation containing paroxetine or a pharmaceutically acceptable salt thereof, and to its use in the treatment and/or prophylaxis of certain disorders.

U.S. Pat. No. 4,007,196 describes inter alia a compound which is commonly known as paroxetine. This compound is a Selective Serotonin Reuptake Inhibitor (SSRI) and is currently marketed world-wide for the treatment and/or prophylaxis of depression.

The current formulation which is the only marketed formulation of paroxetine hydrochloride is a swallow tablet.

It has now been surprisingly found that controlled release and delayed release formulations containing paroxetine give rise to an unexpected reduction in the side effects associated with swallow tablets.

Accordingly, the present invention provides a controlled release or delayed release formulation containing paroxetine or a pharmaceutically acceptable salt thereof.

A further aspect of the invention provides a controlled release or delayed release formulation containing an SSRI. Examples of SSRIs other than paroxetine include fluoxetine (U.S. Pat. No. 4,314,081), fluvoxamine (U.S. Pat. No. 4,085,225), and sertraline (U.S. Pat. No. 4,536,518).

By controlled release is meant any formulation technique wherein release of the active substance from the dosage from is modified to occur at a slower rater than that from an immediate release product, such as a conventional swallow tablet or capsule.

By delayed release is meant any formulation technique wherein release of the active substance from the dosage form is modified to occur at a later time than that from a conventional immediate release product The subsequent release of active substance from a delayed release formulation may also be controlled as defined above.

Examples of controlled release formulations which are suitable for incorporating paroxetine and other SSRIs are described in:

Sustained Release Medications, Chemical Technology Review No. 177. Ed. J. C. Johnson. Noyes Data Corporation 1980.

Controlled Drug Delivery, Fundamentals and Applications, 2nd Edition. Eds. J. R. Robinson, V. H. L. Lee. Mercel Dekkes Inc. New York 1987.

Examples of delayed release formulations which are suitable for incorporating paroxetine and other SSRIs are described in:

Remington's Pharmaceutical Sciences 16th Edition, Mack Publishing Company 1980, Ed. A. Osol.

Such controlled release formulations are preferably formulated in a manner such that release of active substance such as paroxetine is effected predominantly during the passage through the stomach and the small intestine, and delayed release formulations are preferably formulated such that release of active substance such as paroxetine is avoided in the stomach and is effected predominantly during passage through the small intestine.

Said formulations are preferably formulated such that the release of the active substance is predominantly 1½ to 3 hours post ingestion.

The small intestine is suitably the duodenum, the ileum or the jejunem.

Patients who benefit most from the formulations of the present invention are those who are known to suffer from nausea upon oral administration using swallow tablets.

Preferred formulations are ultimately enteric coated tablets or caplets, wax or polymer coated tablets or caplets or time-release matrices, or combinations thereof.

Particularly preferred formulations are described in U.S. Pat. No. 5,102,666.

Thus, a particular aspect of the invention provides a polymeric controlled release composition comprising a reaction complex formed by the interaction of (1) a calcium polycarbophil component which is a water-swellable, but water insoluble, fibrous cross-linked carboxy-functional polymer, said polymer containing (a) a plurality of repeating units of which at least about 80%o contain at least one carboxyl functionality, and (b) about 0.05 to about 1.5% cross-linking agent substantially free from polyalkenyl polyether, said percentages being based upon the weights of unpolymerised repeating unit and cross-linking agent, respectively, with (2) water, in the presence of an active agent selected from the group consisting of SSRIs such as paroxetine. The amount of calcium polycarbophil present is from about 0.1 to about 99% by weight, for example about 10%. The amount of active agent present is from about 0.0001 to about 65% by weight, for example between about 5 and 20%. The amount of water present is from about 5 to about 200% by weight, for example between about 5 and 10%. The interaction is carried out at a pH of between about 3 and about 10, for example about 6 to 7. The calcium polycarbophil is originally present in the form of a calcium salt containing from about 5 to about 25% calcium.

Further particularly preferred formulations are described in U.S. Pat. No. 5,422,123.

Thus, a further particular aspect of the invention provides a system for the controlled release of an active substance which is an SSRI such as paroxetine, comprising (a) a deposit-core comprising an effective amount of the active substance and having defined geometric form, and (b) a support-platform applied to said deposit-core, wherein said deposit-core contains at least the active substance, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

Paroxetine used in the present invention is suitably in the form of the free base or a pharmaceutically acceptable salt thereof. Preferably, paroxetine is suitably in the form of the hydrochloride hemihydrate.

Paroxetine hydrochloride hemihydrate may be prepared according to the procedures generally outlined in U.S. Pat. No. 4,721,723.

Paroxetine in the form of a controlled release or delayed release formulation can be used to treat and prevent the following disorders:

Alcoholism
Anxiety
Depression
Obsessive Compulsive Disorder
Panic Disorder
Chronic Pain
Obesity
Senile Dementia
Migraine
Bulimia
Anorexia
Social Phobia
Pre-Menstrual Syndrome (PMS)
Adolescent Depression
Trichotillomania
Dysthymia
Substance Abuse These disorders are herein after referred to as "the disorders".

The present invention provides a method of treating and/or preventing the disorders by administering an effective and/or a prophylactic amount of a controlled release or delayed release formulation containing paroxetine or a pharmaceutically acceptable salt thereof, to a sufferer in need thereof.

The present invention further provides the use of a controlled release or delayed release formulation containing paroxetine or a pharmaceutically acceptable salt thereof in the manufacture of a medicament, for treating and/or preventing the disorders.

The present invention also provides a pharmaceutical composition for use in the treatment and/or prevention of the disorders which comprises a controlled release or delayed release formulation containing paroxetine or a pharmaceutically acceptable salt thereof.

The following examples illustrate the present invention.

Example 1 (Hydrophilic Matrix)

| | % w/w |
|---|---|
| Intragranular | |
| Paroxetine Hydrochloride | 11.45 |
| Methocel E5 | 1.25 |
| Lactose | 12.3 |
| Extragranular | |
| Methocel K100LV | 30.0 |
| Lactose | 44.0 |
| Magnesium Stearate | 1.0 |
| TOTAL | 100.0 |

Example 2 (Hydrophilic Matrix)

| | % w/w |
|---|---|
| Intragranular | |
| Paroxetine Hydrochloride | 11.45 |
| Methocel E5 | 1.25 |
| Lactose | 12.3 |
| Extragranular | |
| Methocel K100LV | 27.5 |
| Methocel K4M | 7.5 |
| Lactose | 39.0 |
| Magnesium Stearate | 1.0 |
| TOTAL | 100.0 |

Example 3 (pH Sensitive Coat on Immediate Release Core)

| | % w/w |
|---|---|
| Tablet Core | |
| Paroxetine Hydrochloride | 11.45 |
| Lactose | 64.05 |
| Microcrystalline Cellulose | 20.0 |
| Sodium Starch Glycollate | 4.0 |
| Magnesium Stearate | 0.5 |
| TOTAL | 100.0 |

Tablet Coating (apply approximately 6–10% of tablet core weight)

| | % w/w |
|---|---|
| Hydroxypropylmethylcellulose Phthalate | 90.0 |
| Triacetin | 10.0 |

Example 4 (pH Sensitive Coat on Immediate Release Core)

| | % w/w |
|---|---|

Tablet Core as in Example 3
Tablet Coating (apply approximately 6–10% of tablet core weight)

| | % w/w |
|---|---|
| Cellulose Acetate Phthaulate | 90.0 |
| Diethyl Phthalate | 10.0 |

Example 5 (Controlled Release Coating on Immediate Release Core)

| | % w/w |
|---|---|

Tablet Core as in Example 3
Tablet Coating (apply approximately 5–12% of tablet core weight)

| | % w/w |
|---|---|
| Eudragit RS 100 | 86.0 |
| Dibutyl Phthalate | 10.0 |
| Talc | 4.0 |
| FD&C Yellow No.6 | 0.01 |

Example 6 (pH Sensitive Coat on Controlled Release Core.)

Tablet Core as in Example 3
Tablet Coating as in Example 3

Example 7 (Encapsulated Controlled Release Coated Beads)

| | % w/w (approx) |
|---|---|
| Pellet | |
| Non Pareil Seed | 30 |
| Paroxetine Hydrochloride | 40 |
| Gelatin | 8 |
| Lactose | 20 |
| Talc | 2 |

| | % w/w |
|---|---|
| Coating | |
| Glycerylmonostearate | 36.6 |
| Glyceryldistearate | 53.4 |
| White Wax | 10.0 |

Example 8 (Controlled release bilayer tablet)

| Component | mg/tablet | Function |
|---|---|---|
| Active Layer | | |
| Paroxetine Hydrochloride | 22.89* | Active |
| Methocel K4M | 15.00 | Hydrogel polymer |
| Lactose monohydrate | 62.0 | Hydrophilic agent |
| Polyvinylpyrrolidone | 3.0 | Binder |
| Magnesium stearate | 1.0 | Hydrophobic agent |
| Syloid 244 | 1.0 | Hydrophilic agent |
| Support platform | | |
| Compritol 888 | 15.04 | Plasticizer |
| Lactose monohydrate | 29.32 | Hydrophilic agent |
| Polyvinylpyrrolidone | 4.0 | Binder |
| Magnesium stearate | 1.52 | Hydrophobic agent |
| Methocel E5 | 29.32 | Hydrogel polymer |
| Iron oxide | 0.08 | Colourant |
| Total tablet weight | 184.89 mg | |

*Equivalent to 20 mg paroxetine as free base.

The powder blend for each layer was wet granulated in a high shear mixer/granulator and dried in a fluid bed drier. The bilayer tablets were compressed on a Manesty triple layer press.

Example 9 (Enteric coated calcium polycarbophil formulation)

| Component | mg/tablet | Function |
|---|---|---|
| Core | | |
| Paroxetine Hydrochloride | 22.89* | Active |
| Calcium polycarbophil | 20.00 | Matrix |
| Lactose anhydrous | 146.11 | Hydrophilic agent/diluent |
| Polyvinylpyrrolidone | 10.0 | Binder |
| Magnesium stearate | 1.0 | Hydrophobic agent/lubricant |
| Water** | 0.024 | Granulating liquid |
| Enteric coat | | |
| Eudragit | 22.19 | Polymer |
| Talc | 1.53 | Lubricant |
| Triethyl citrate | 1.00 | Plasticizer |
| Water** | 24.6 | Diluent |
| Film coat | | |
| Opadry pink | 10.5 | Film coat |
| Water** | 94.5 | Diluent |
| Polish coat | | |
| Opadry clear | 0.750 | |
| Water** | 29.3 | Diluent |

*Equivalent to 20 mg paroxetine as free base.
**Removed during processing.

The core constituents were wet granulated in a high shear mixer/granulator, and dried in a fluid bed drier. The magnesium stearate was then added and the mixture processed in a low shear mixer. The mix was then compressed on a B type rotary tablet press. Coating was carried out using an Accela cota.

Example 10 (Controlled release bilayer tablet)

| Component | mg/tablet | Function |
|---|---|---|
| Active Layer | | |
| Paroxetine Hydrochloride | 22.89* | Active |
| Methocel K4M | 20.00 | Hydrogel polymer |
| Lactose monohydrate | 60.0 | Hydrophilic agent |
| Polyvinylpyrrolidone | 5.0 | Binder |
| Magnesium stearate | 1.0 | Hydrophobic agent |
| Syloid 244 | 1.0 | Hydrophilic agent |
| Support platform | | |
| Compritol 888 | 14.72 | Plasticizer |
| Lactose monohydrate | 30.60 | Hydrophilic agent |
| Polyvinylpyrrolidone | 2.80 | Binder |
| Magnesium stearate | 0.80 | Hydrophobic agent |
| Methocel E5 | 30.60 | Hydrogel polymer |
| Syloid 244 | 0.40 | Hydrophilic agent |
| Iron oxide | 0.08 | Colourant |
| Total tablet weight | 189.89 mg | |

*Equivalent to 20 mg paroxetine as free base.

The process was as described in Example 8.

Example 11 (Controlled release bilayer tablet)

| Component | mg/tablet | Function |
|---|---|---|
| Active Layer | | |
| Paroxetine Hydrochloride | 22.89* | Active |
| Methocel K4M | 15.00 | Hydrogel polymer |
| Lactose monohydrate | 63.31 | Hydrophilic agent |
| Polyvinylpyrrolidone | 2.0 | Binder |
| Magnesium stearate | 1.0 | Hydrophobic agent |
| Syloid 244 | 0.40 | Hydrophilic agent |
| Support platform- as in Example 10. | | |
| Total tablet weight | 184.60 mg | |

*Equivalent to 20 mg paroxetine as free base.

The process was as described in Example 8.

Example 12 (Enteric coated controlled release bilayer tablet)

| Component | mg/tablet | Function |
|---|---|---|
| Active Layer | | |
| Paroxetine Hydrochloride | 28.61* | Active |
| Methocel K4M | 18.75 | Hydrogel polymer |
| Lactose monohydrate | 79.14 | Hydrophilic agent |
| Polyvinylpyrrolidone | 2.50 | Binder |
| Magnesium stearate | 1.25 | Hydrophobic agent |
| Syloid 244 | 0.50 | Hydrophiic agent |
| Support platform | | |
| Compritol 888 | 15.04 | Plasticizer |
| Lactose monohydrate | 30.50 | Hydrophilic agent |
| Polyvinylpyrrolidone | 4.00 | Binder |
| Magnesium stearate | 0.80 | Hydrophobic agent |
| Methocel E5 | 29.32 | Hydrogel polymer |
| Syloid 244 | 0.32 | Hydrophilic agent |
| Iron oxide | 0.02 | Colourant |
| Enteric coating | | |
| Eudragit | 13.27 | Polymer |
| Talc | 3.31 | Lubricant |
| Triethyl citrate | 1.33 | Plasticizer |
| Water** | 36.25 | Diluent |
| Total tablet weight | 228.66 mg | |

*Equivalent to 25 mg paroxetine as free base.
**Removed during processing.

The process was as described in Example 9.

EXAMPLE 13

GI Tolerance Study

The design of the study is outlined below

| | |
|---|---|
| Subjects: | Normal healthy volunteers |
| Design: | Parallel group, placebo controlled, double blind |
| Treatment: | (a) Placebo, (b) Immediate release paroxetine, (c) Example 8 formulation, (d) Example 8 formulation with enteric coating. |
| Dosage: | 30 mg once daily for 3 days |
| Number of subjects: | 452 evaluable (488 randomised, 485 evaluable) |

The study was conducted to compare the incidence, severity and duration of nausea and vomiting, and diarrhoea (theoretically if the controlled release formulations slow down absorption of paroxetine then, as paroxetine is known to be prokinetic to the GI tract there may be an increased incidence).

Adverse experiences (AE) information was assessed each morning at the time of dosing and again 24 hours following the last dose. Investigators and subjects were given diary cards detailing how to classify severity of AEs in order to standardise as much as possible across all 6 centres.

Of the 485 evaluable subjects, 18 (3.7%) withdrew, 17 because of adverse events. Subjects with nausea/vomiting on the day of withdrawal were more common on (b) than either of (c) and (d).

The incidence of nausea/vomiting and diarrhoea is shown in the table below:

| | (b) | (c) | (d) | Placebo |
|---|---|---|---|---|
| Incidence of nausea | 59% | 49% | 39% | 13% |
| Incidence of diarrhoea | 15% | 21% | 20% | 7% |

The incidence of nausea was increased for both (b) and placebo compared to the expected rates of approximately 25% and 5% respectively for volunteers at these dosages for 3 days duration. The overall incidence of nausea was less on (c) and (d) than on (b). The severity of nausea was also decreased as shown in the next table.

| Nausea severity | (b) | (c) | (d) | Placebo |
|---|---|---|---|---|
| None | 50 (41%) | 63 (52%) | 74 (61%) | 104 (87%) |
| Mild | 45 (37%) | 40 (33%) | 30 (25%) | 16 (13%) |
| Moderate | 21 (17%) | 17 (14%) | 15 (12%) | 0 (0%) |
| Severe | 6 (5%) | 1 (1%) | 3 (2%) | 0 (0%) |

Severity of diarrhoea is reported in the table below:

| Severity of diarrhoea | (b) | (c) | (d) | Placebo |
|---|---|---|---|---|
| None | 104 (85%) | 95 (79%) | 97 (80%) | 112 (93%) |
| Mild | 16 (13%) | 16 (13%) | 16 (13%) | 8 (7%) |
| Moderate | 1 (1%) | 8 (7%) | 9 (1%) | 0 (0%) |
| Severe | 1 (1%) | 2 (2%) | 0 (0%) | 0 (0%) |

In conclusion, there appears to be a trend for (c) to reduce the incidence of nausea and the dropout rate due to adverse events in comparison to (b), but analysis of the results was complicated by a statistically significant treatment-by-centre difference. (d) shows a halving in the dropout rate and a fall in incidence of nausea of 20% (a proportional fall of 33%). In addition there is a reduction in severity of nausea of those individuals who report nausea on (c) and (d). There is an increase in incidence of diarrhoea on both of (c) and (d) in relation to (b), but this is confined to an increase in the number of individuals reporting moderate diarrhoea and there is no increase in those with severe diarrhoea.

What is claimed is:

1. A composition, that reduces the incidence of nausea and vomiting associated with the administration of paroxetine, comprising paroxetine, or a pharmaceutically acceptable salt thereof, in a controlled and delayed release swallow pharmaceutical formulation that, upon administration, releases the paroxetine predominantly in the small intestine.

2. A method of treating one or more disease states selected from; Alcoholism, Anxiety, Depression, Obsessive Compulsive Disorder, Panic Disorder, Chronic Pain, Obesity, Senile Dementia, Migraine, Bulimia, Anorexia, Social Phobia, Pre-Menstrual Syndrome (PMS), Adolescent Depression, Trichotillomania, Dysthymla and Substance Abuse, which comprises administering an effective amount of a controlled and delayed release swallow pharmaceutical formulation that, upon administration, releases paroxetine or a pharmaceutically acceptable salt thereof, predominantly in the small intestine to an individual in need thereof.

* * * * *